(12) United States Patent
Tanaka et al.

(10) Patent No.: US 8,592,470 B2
(45) Date of Patent: Nov. 26, 2013

(54) SITAXENTAN DERIVATIVE

(71) Applicant: Eisai R&D Management Co., Ltd., Tokyo (JP)

(72) Inventors: Keigo Tanaka, Tsukuba (JP); Tomoki Nishioka, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/752,660

(22) Filed: Jan. 29, 2013

(65) Prior Publication Data

US 2013/0197045 A1    Aug. 1, 2013

Related U.S. Application Data

(60) Provisional application No. 61/592,923, filed on Jan. 31, 2012.

(51) Int. Cl.
*C07D 413/14* (2006.01)

(52) U.S. Cl.
USPC .......................................... 514/380; 548/246

(58) Field of Classification Search
None
See application file for complete search history.

(56) References Cited

FOREIGN PATENT DOCUMENTS

WO    WO 96/31492       10/1996
WO    WO 2008/124803    10/2008

OTHER PUBLICATIONS

Written Opinion for PCT/JP2013/051857, May 7, 2013 (and English translation thereof).
Bertelsen et al., "Apparent mechanism-based inhibition of human CYP2D6 in vitro by paroxetine: comparison with fluoxetine and quinidine," *Drug Metab Dispos.*, Mar. 2003, 31(3):289-293.
Blagg, "Structural alerts for toxicity", Burger's Medicinal Chemistry, Drug Discovery and Development, 7th Edition, edited by Abraham and Rotella, Aug. 2010, pp. 301-334.
Fontana et al., "Cytochrome p450 enzymes mechanism based inhibitors: common sub-structures and reactivity," *Curr Drug Metab.* Oct. 2005, 6(5):413-454.
Murray et al., "Selectivity in the inhibition of mammalian cytochromes P-450 by chemical agents," *Pharmacol Rev.* Jun. 1990, 42(2):85-101.
Wu, "Recent discovery and development of endothelin receptor antagonists.", *Exp Opin Ther*, Patents, Nov. 2000, 10(11):1653-1668.

*Primary Examiner* — Kamal Saeed
(74) *Attorney, Agent, or Firm* — Fish & Richardson P.C.

(57) ABSTRACT

A compound represented by formula (1-1) or (1-2), or a pharmacologically acceptable salt thereof retains the principal therapeutic effect of sitaxentan and has an improved CYP inhibitory effect:

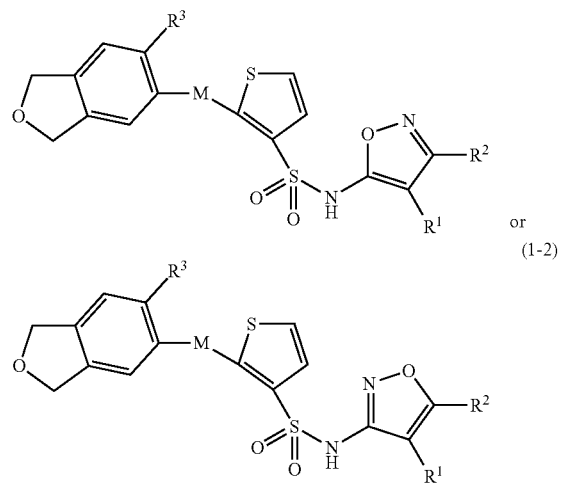

wherein $R^1$ is a halogen atom, etc., $R^2$ is a methyl group, etc., $R^3$ is a $C_{1-6}$ alkyl group, etc., and M is a group represented by:

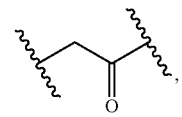

etc.

16 Claims, 3 Drawing Sheets

SITAXENTAN DERIVATIVE

CROSS-REFERENCE TO RELATED APPLICATION

This application claims the benefit of U.S. provisional application No. 61/592,923 filed on Jan. 31, 2012, the disclosure of which is herein incorporated by reference in its entirety.

TECHNICAL FIELD

The present invention relates to a compound having a phthalan ring. More specifically, it relates to N-(4-chloro-3-methyl-1,2-oxazol-5-yl)-2-[2-(6-methyl-1,3-dihydro-2-benzofuran-5-yl)acetyl]thiophene-3-sulfonamide and its analogs.

BACKGROUND ART

Thienyl sulfonamide compounds are known as endothelin receptor antagonists. For example, sitaxentan, also known as N-(4-chloro-3-methyl-1,2-oxazol-5-yl)-2-[2-(6-methyl-2H-1,3-benzodioxol-5-yl)acetyl]thiophene-3-sulfonamide, is a compound that has been marketed for the effectiveness for pulmonary arterial hypertension and other conditions (Patent Literature 1).

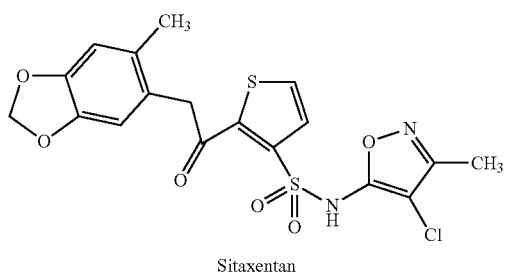 [SMILES: Cc1cc2c(cc1CC(=O)c1sccc1S(=O)(=O)Nc1onc(C)c1Cl)OCO2]

Sitaxentan

However, the structure of sitaxentan includes a benzodioxol ring, and in general, compounds having such benzodioxol rings are converted to chemically highly reactive metabolites when metabolized by cytochrome P450 (CYP), and are known to irreversibly inhibit the activity of CYP by inactivation based on the covalent binding with CYP (Non Patent Literatures 1-3). Sitaxentan itself is known to have CYP inhibitory activity, and there have been several reports of drug-drug interactions with clinically used medications. To solve this problem, a compound has been developed having a deuterium atom substituted for a hydrogen atom on the methylene carbon of the benzodioxolyl group of sitaxentan, but no such compound is yet in commercial use, and the effects have been unsatisfactory (Patent Literature 2). Also, it is known that compounds containing deuterium generally require higher production costs. As a consequence, to solve this problem there is a need for a method that does not use deuterium.

CITATION LIST

[Patent Literature 1] WO 96/31492
[Patent Literature 2] WO 2008/124803
[Non Patent Literature 1] Pharmacological reviews 42, 85, 1990 (Selectivity in the inhibition of Mammalian Cytochrome P-450 by Chemical Agents)
[Non Patent Literature 2] Current Drug Metabolism, 6, 413, 2005
[Non Patent Literature 3] Drug Metabolism and Disposition 31, 289, 2003
[Non Patent Literature 4] Burger's Medicinal Chemistry, Drug Discovery and Development, 7th Edition, edited by Abraham and Rotella, August 2010, "STRUCTURAL ALERTS FOR TOXICITY" by Blagg, p 301-334
[Non Patent Literature 5] Exp Opin Ther Patents, 10, 1653-1668, 2000

SUMMARY OF INVENTION

Technical Problem

It is an object of the present invention to provide a compound retaining the principal therapeutic effect of sitaxentan and having an improved CYP inhibitory effect as well as having a structure that contains no deuterium.

Solution to Problem

As a result of intensive studies, the present inventors have found the present invention. Specifically, the present invention relates to the following [1] to [19]
[1] A compound represented by formula (1-1) or formula (1-2), or a pharmacologically acceptable salt thereof.

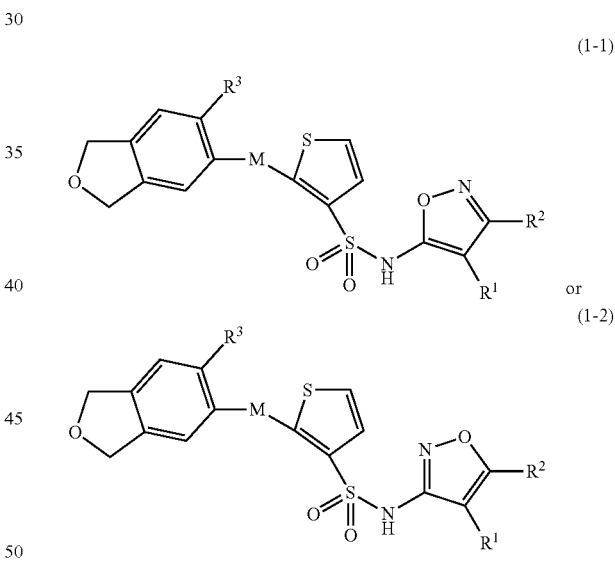

wherein $R^1$ is a halogen atom, a methyl group, an ethyl group, a trifluoromethyl group, a pentafluoroethyl group, an n-propyl group or a cyclopropyl group, $R^2$ is a hydrogen atom, a methyl group, an ethyl group, a trifluoromethyl group, a pentafluoroethyl group, an n-propyl group or a cyclopropyl group, $R^3$ is a $C_{1-6}$ alkyl group or a $C_{1-6}$ alkoxy group, and M is a group selected from the group consisting of:

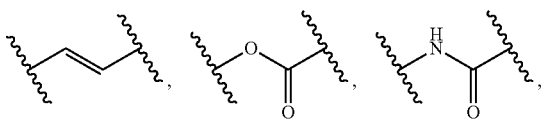

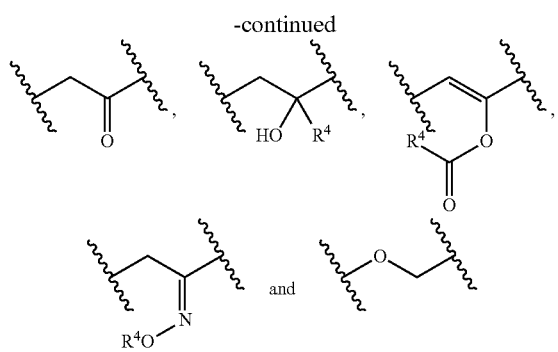

wherein R⁴ is a hydrogen atom, a methyl group or an ethyl group.

[2] The compound or pharmacologically acceptable salt thereof according to [1], wherein M is a group represented by the following formula:

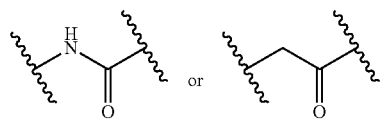 [SMILES: *NC(*)=O ; *CC(*)=O]

[3] The compound or pharmacologically acceptable salt thereof according to [1], wherein M is a group represented by the following formula:

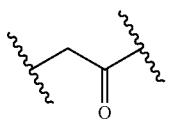 [SMILES: *CC(*)=O]

[4] The compound or pharmacologically acceptable salt thereof according to any one of [1] to [3], wherein R¹ is a halogen atom.
[5] The compound or pharmacologically acceptable salt thereof according to [4], wherein R¹ is a chlorine atom.
[6] The compound or pharmacologically acceptable salt thereof according to any one of [1] to [5], wherein R² is a methyl group.
[7] The compound or pharmacologically acceptable salt thereof according to any one of [1] to [6], wherein R³ is a $C_{1-6}$ alkyl group.
[8] The compound or pharmacologically acceptable salt thereof according to [7], wherein R³ is a methyl group.
[9] The compound or pharmacologically acceptable salt thereof according to any one of [1] to [8], which is a compound represented by formula (1-1).
[10] N-(4-Chloro-3-methyl-1,2-oxazol-5-yl)-2-[2-(6-methyl-1,3-dihydro-2-benzofuran-5-yl)acetyl]thiophene-3-sulfonamide or a pharmacologically acceptable salt thereof.
[11] A pharmaceutical composition comprising the compound or pharmacologically acceptable salt thereof according to any one of [1] to [10].
[12] The pharmaceutical composition according to [11], which is an endothelin receptor antagonist.
[13] The pharmaceutical composition according to [11], which is a therapeutic or preventative agent for pulmonary arterial hypertension.
[14] A method of antagonizing an endothelin receptor comprising administering the compound or pharmacologically acceptable salt thereof according to any one of [1] to [10] to a patient.
[15] A method of treating or preventing pulmonary arterial hypertension comprising administering the compound or pharmacologically acceptable salt thereof according to any one of [1] to [10] to a patient
[16] A compound or pharmacologically acceptable salt thereof according to any one of [1] to [10] for use for antagonizing an endothelin receptor.
[17] A compound or pharmacologically acceptable salt thereof according to any one of [1] to [10] for use for treating or preventing pulmonary arterial hypertension.
[18] Use of the compound or pharmacologically acceptable salt thereof according to any one of [1] to [10] for the manufacture of an endothelin receptor antagonist.
[19] Use of the compound or pharmacologically acceptable salt thereof according to any one of [1] to [10] for the manufacture of a therapeutic or preventative agent for pulmonary arterial hypertension.

Advantageous Effects of Invention

The compound represented by formula (1-1) or (1-2) (hereunder called Compound (1-1) or Compound (1-2), or collectively called Compound (1)) retains the principal therapeutic effect of sitaxentan and having an improved CYP inhibitory effect compared to sitaxentan.

DESCRIPTION OF EMBODIMENTS

Figure 1:
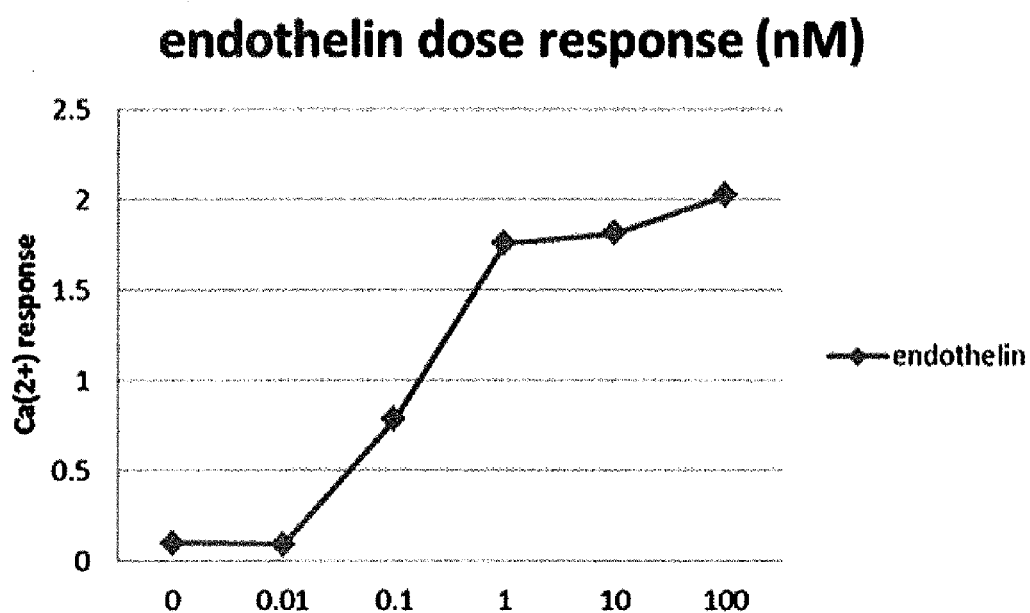
FIG. 1 is a graph showing dose-dependent activation ($Ca^{2+}$ elevation) by a ligand (endothelin) in EDNRA/293 cells, with activation ($Ca^{2+}$ elevation) shown on the vertical axis and endothelin concentration (nM) on the horizontal axis.

The present invention will be described in detail below.

In the present specification, the present invention is not limited to a particular crystal form but may include any one of crystal forms or mixtures thereof; although crystal polymorphs may exist. The present invention also includes amorphous forms, and the compounds according to the present invention include anhydrides and hydrates.

The meanings of the terms, symbols and the like used in the present specification are explained below, and the present invention is explained in detail.

"CYP" in the present specification is the drug-metabolizing enzyme Cytochrome P450.

"Improve CYP inhibitory effect" or "improved CYP inhibitory effect" in the present specification means that the degree of inhibition of one or two among five CYP molecules (CYP1A2, 2C9, 2C19, 2D6 and 3A4), the major CYP molecules, is generally improved than that of sitaxentan.

"Retains the principal therapeutic effect" in the present specification means that showing in vitro or in vivo pharmacological activity in preclinical study, which is expected to show clinical therapeutic effect as sitaxentan does. In vitro pharmacological activity means, for example, suppression activity with respect to endothelin receptor A.

"$IC_{50}$" in the present specification means the 50% inhibition concentration or half inhibition concentration.

The "benzodioxol ring" in the present specification is a ring or functional group having the following structure:

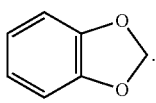

The "phthalan ring" in the present specification means a ring or functional group having the following structure:

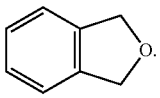

The "halogen atom" in the present specification means a fluorine atom, a chlorine atom, a bromine atom or an iodine atom.

The "$C_{1-6}$ alkyl group" in the present specification means a linear or branched alkyl group having 1 to 6 carbon atoms, and examples include a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 1-hexyl group, a 2-hexyl group and a 3-hexyl group.

The term "$C_{1-6}$ alkoxy group" used in the present specification means a group in which an oxygen atom is attached to the end of the above-defined "C1-6 alkyl group", and examples include a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 1-hexyloxy group, a 2-hexyloxy group and a 3-hexyloxy group.

The compound of the present invention is a compound represented by formula (1-1) or formula (1-2), and is preferably a compound represented by formula (1-1).

$R^1$ in the compound represented by formula (1-1) or (1-2) is a halogen atom, a methyl group, an ethyl group, a trifluoromethyl group, a pentafluoroethyl group, an n-propyl group or a cyclopropyl group, and $R^1$ is preferably a halogen atom and more preferably a chlorine atom.

$R^2$ in the compound represented by formula (1-1) or (1-2) is a hydrogen atom, a methyl group, an ethyl group, a trifluoromethyl group, a pentafluoroethyl group, an n-propyl group or a cyclopropyl group, and $R^2$ is preferably a methyl group.

$R^3$ in the compound represented by formula (1-1) or (1-2) is a $C_{1-6}$ alkyl group or a $C_{1-6}$ alkoxy group, and $R^3$ is preferably a $C_{1-6}$ alkyl group and more preferably a methyl group.

M in the compound represented by formula (1-1) or (1-2) is a group selected from the group consisting of:

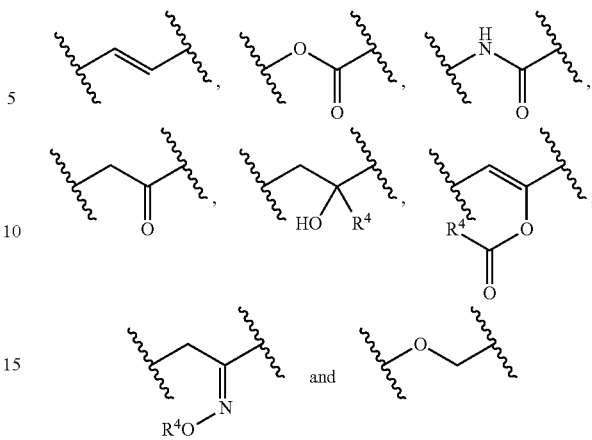

wherein $R^4$ is a hydrogen atom, a methyl group or an ethyl group. The bonds in the groups shown above are oriented with the left-hand radical bound to the phthalan ring and the right-hand radical bound to the thiophene ring. M is preferably a group represented by:

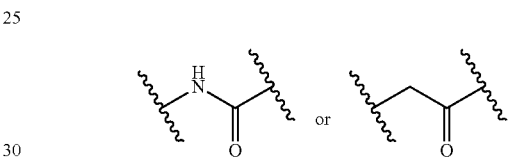

with the carbonyl carbon bound to the thiophene ring, and more preferably a group represented by:

with the carbonyl carbon bound to the thiophene ring.

The "pharmacologically acceptable salt" in the present specification is not particularly limited insofar as it forms a salt with the compound represented by formula (1-1) or (1-2) and is pharmacologically acceptable, and examples include inorganic acid salts, organic acid salts, inorganic base salts, organic base salts, and acidic or basic amino acid salts.

Preferred examples of inorganic acid salts include hydrochlorides, hydrobromides, sulfates, nitrates and phosphates, and preferred examples of organic acid salts include acetates, succinates, fumarates, maleates, tartrates, citrates, lactates, stearates, benzoates, mandelates, methanesulfonates, ethanesulfonates, p-toluenesulfonates and benzenesulfonates.

Preferred examples of inorganic base salts include alkali metal salts such as sodium salts and potassium salts, alkaline earth metal salts such as calcium salts and magnesium salts, aluminum salts and ammonium salts, and preferred examples of organic base salts include diethylamine salts, diethanolamine salts, meglumine salts and N,N'-dibenzylethylenediamine salts.

Preferred examples of acidic amino acid salts include aspartates and glutamates, and preferred examples of basic amino acid salts include arginine salts, lysine salts and ornithine salts.

The compound represented by formula (1-1) or (1-2) can be produced by the methods described below, or by the methods described below with improvements made based on ordinary knowledge by a person skilled in the art. However, the method for producing the compound represented by formula (1-1) or (1-2) is not limited to these.

Process A

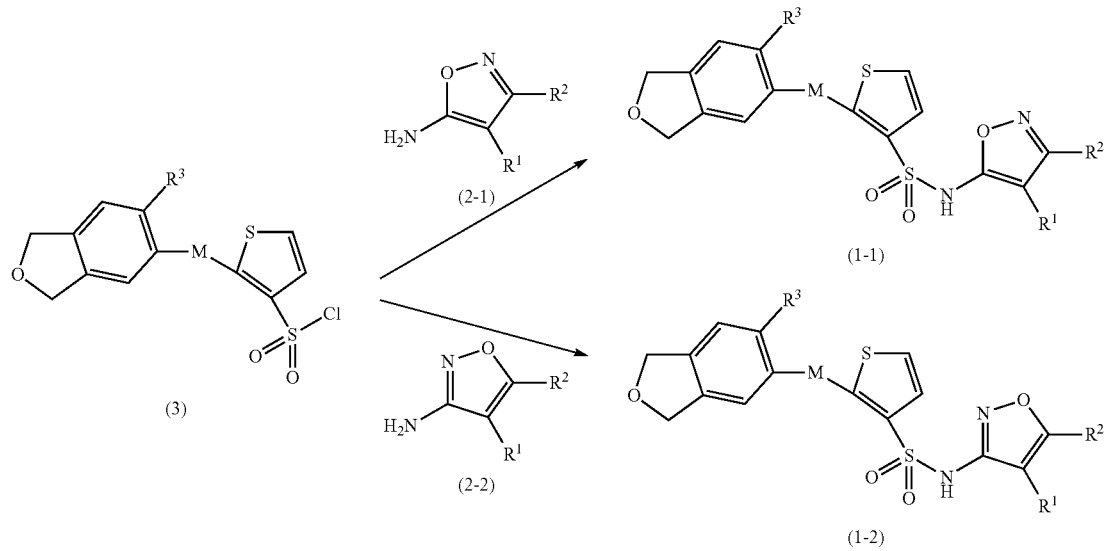

wherein $R^1$, $R^2$, $R^3$ and M are as defined above.

This process is a process whereby Compound (1-1) or (1-2) is obtained by a condensation reaction of a sulfonyl chloride compound (3) with an amino isoxazole compound (2-1) or (2-2) in the presence or absence of a solvent, in the presence of a base, and in the presence or absence of a catalyst.

The solvent used is not particularly limited as long as it dissolves the starting materials to a certain extent without inhibiting the reaction, and includes, for example, tetrahydrofuran and pyridine.

The base used includes, for example, sodium hydride or pyridine.

4-Dimethyl aminopyridine or the like can be used as the catalyst.

The reaction temperature differs according to the starting materials, the solvent and the like, but is normally 0° C. to 120° C., and preferably 15° C. to 100° C.

The reaction time differs depending on the starting materials, the solvent and the like, but is normally 10 minutes to 5 days, and preferably 1 hour to 3 days.

The sulfonyl chloride compound (3) and amino isoxazole compound (2-1) or (2-2) may be commercial products, or those described in the following examples may be used, or the compounds may be synthesized by methods known to those skilled in the art (for example, U.S. Pat. Nos. 4,659,369, 4,861,366, 4,753,672).

Process B

When M in Compound (1-1) or (1-2) is the group represented by:

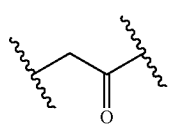 [SMILES: *CC(*)=O]

Compound (1-1) or (1-2) can be obtained by Process B below. The scheme below is explained as a method for producing Compound (1-1), but Compound (1-2) can be obtained in the same way using different starting materials.

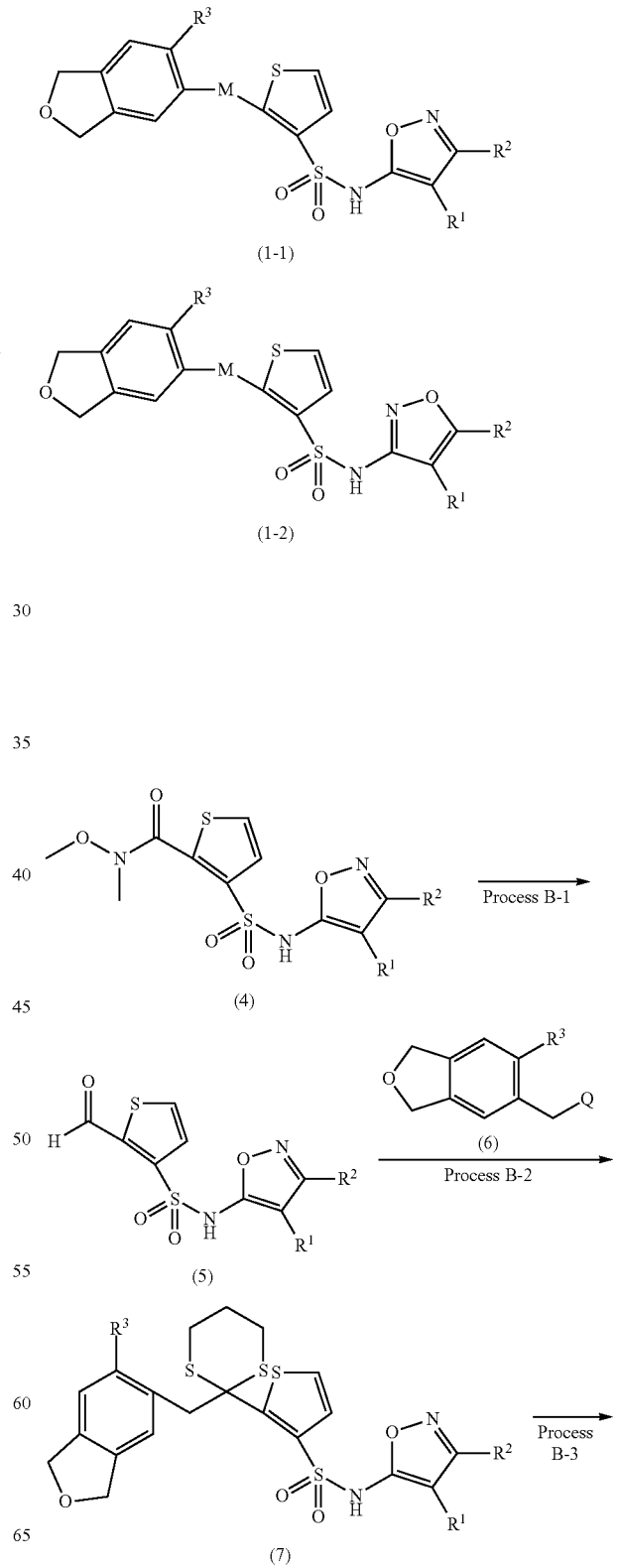

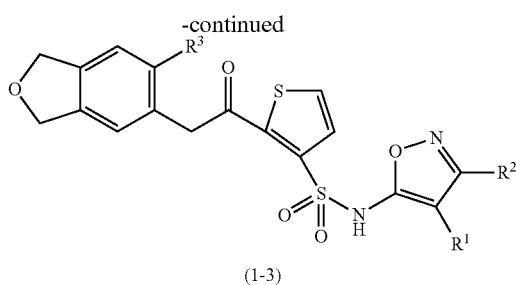

(1-3)

wherein $R^1$, $R^2$ and $R^3$ are defined as before; and Q is a leaving group including a halogen atom such as a bromine atom, a chlorine atom and an iodine atom, a $C_{1-4}$ alkanesulfonyloxy group such as a methanesulfonyloxy group and a sulfonyloxy group such as a benzenesulfonyloxy group and p-toluenesulfonyloxy group.

Compound (4) and Compound (6) may be known compounds, or may be compounds that can be produced by ordinary methods by a person skilled in the art from known compounds.

Process B-1

This process is a process of converting Compound (4) into Compound (5) using a reducing agent in the presence of a solvent.

The solvent used is not particularly limited as long as it dissolves the starting materials to a certain extent without inhibiting the reaction, and includes, for example, tetrahydrofuran.

The reducing agent used includes, for example, diisobutyl aluminum hydride.

The reaction temperature differs according to the starting materials, the solvent and the like, but is normally −78° C. to 100° C., and preferably −78° C. to room temperature.

The reaction time differs according to the starting materials, the solvent and the like, but is normally 10 minutes to 5 days, and preferably 30 minutes to 1 day.

Process B-2

This process is a process of first converting the formyl group of Compound (5) to dithiane with 1,3-propanedithiol, then using a base to generate anions in the dithiane, and then reacting this with Compound (6) to obtain Compound (7). A Lewis acid may also be added to obtain better results during conversion to dithiane.

The solvent used in the conversion reaction to dithiane is not particularly limited as long as it dissolves the starting materials to a certain extent without inhibiting the reaction, but includes, for example, dichloromethane.

The Lewis acid used in the conversion reaction to dithiane includes, for example, boron trifluoride diethyl etherate.

The reaction temperature for the conversion reaction to dithiane differs according to the starting materials, the solvent and the like, but is normally 0° C. to 100° C., and preferably room temperature.

The reaction time for the conversion reaction to dithiane differs according to the starting raw materials, the solvent and the like, but is normally 10 minutes to 5 days, and preferably 30 minutes to 1 day.

The solvent used for anion generation and the reaction with Compound (6) is not particularly limited as long as it dissolves the starting materials to a certain extent without inhibiting the reaction, but includes, for example, tetrahydrofuran.

The base used for anion generation and the reaction with Compound (6) includes, for example, n-butyl lithium.

The reaction temperature differs according to the starling materials, the solvent and the like, but is normally −78° C. to 100° C., and preferably −78° C. to room temperature.

The reaction time differs according to the starting materials, the solvent and the like, but is normally 10 minutes to 5 days, and preferably 30 minutes to 1 day.

Process B-3

The process is a process of converting the dithaine ring of Compound (7) to a carbonyl group to obtain Compound (1-3), or in other words Compound (1-1) in which M is the group represented by:

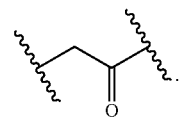 [SMILES: *CC(*)=O]

This process can be accomplished by means of an ordinary dithiane ring deprotection reaction, for example a reaction with oxidizing agent such as a silver nitrate.

The solvent used in the dithiane ring deprotection reaction is not particularly limited as long as it dissolves the starting materials to a certain extent without inhibiting the reaction, but includes, for example, methanol, water and tetrahydrofuran.

The oxidizing agent used in the dithiane ring deprotection reaction includes, for example, silver nitrate.

The reaction temperature for the dithiane ring deprotection reaction differs according to the starting materials, the solvent and the like, but is normally 0° C. to 150° C., and preferably room temperature to 100° C.

The reaction time for the dithiane ring deprotection reaction differs according to the starting materials, the solvent and the like, but is normally 30 minutes to 5 days, and preferably 1 day to 4 days.

After completion of the reaction in each process of each method described above, the target compound in each process can be collected from the reaction mixture according to a conventional method.

For example, when the whole reaction mixture is a liquid, the reaction mixture is cooled to room temperature or cooled with ice as desired, and neutralized with an acid, alkali, oxidizing agent or reducing agent as appropriate, an organic solvent immiscible with water and not reactive with the target compound such as ethyl acetate is added, and the layer containing the target compound is separated. Next, a solvent immiscible with the resulting layer and not reactive with the target compound is added, the layer containing the target compound is washed, and the layer is separated. Moreover, when the layer is an organic layer, the target compound can be collected by drying with a drying agent such as anhydrous magnesium sulfate or anhydrous sodium sulfate and distilling off the solvent. When the layer is an aqueous layer, the target compound can be collected by electrically demineralizing and then lyophilizing the layer.

In addition, when the whole reaction mixture is a liquid and if possible, the target compound can be collected only by distilling off substances other than the target compound (such as a solvent or a reagent) under normal pressure or reduced pressure.

Further, when only the target compound is precipitated as a solid, or when the whole reaction mixture described above is a liquid and only the target compound is precipitated in the course of collection, the target compound can be further collected by collecting the target compound by filtration first, washing the target compound collected by filtration with an appropriate organic or inorganic solvent and drying, such that the mother liquor is treated in a manner similar to the case where the whole reaction mixture described above is a liquid.

Still further, when only the reagent or catalyst is present as a solid, or the whole reaction mixture described above is a liquid and only the reagent or catalyst is precipitated as a solid in the course of collection, and the target compound is dissolved in the solution, the target compound can be collected by filtering off the reagent or catalyst first, washing the reagent or catalyst filtered off with an appropriate organic or inorganic solvent, combining the resulting washings with the mother liquor, and treating the resulting mixture in a manner similar to the case where the whole reaction mixture described above is a liquid.

In particular, when substances other than the target compound which are contained in the reaction mixture do not inhibit the reaction in the next step, the reaction mixture may also be used in the next step as is without particularly isolating the target compound.

Recrystallization, various chromatography methods and distillation may be carried out as appropriate in order to improve the purity of the target compound collected by the above method.

Typically, when the collected target compound is a solid, the purity of the target compound can be improved by recrystallization. In recrystallization, a single solvent or a mixture of a plurality of solvents not reactive with the target compound may be used. Specifically, the target compound is first dissolved in one or more solvents not reactive with the target compound at room temperature or under heating. The resulting mixture is cooled with ice water or the like or is stirred or left to stand at room temperature, such that the target compound can be crystallized from the mixture.

The purity of the collected target compound can be improved by various chromatography methods. Generally, it is possible to use weak acidic silica gels such as Silica gel 60 manufactured by Merck KGaA (70-230 mesh or 340-400 mesh) and BW-300 manufactured by Fuji Silysia Chemical Ltd. (300 mesh). When the target compound is basic and is adsorbed onto the above silica gels too strongly, it is also possible to use NH silica gels such as propylamine coated silica gel manufactured by Fuji Silysia Chemical Ltd. (200-350 mesh) and disposable medium pressure preparative packed column manufactured by Yamazen Corporation (Hi-Flash Amino). When the target compound is dipolar or must be eluted with a more polar solvent such as methanol, for example, it is also possible to use NAM-200H or NAM-300H manufactured by NAM Laboratory or YMC GEL ODS-A manufactured by YMC Co. Ltd. It is also possible to use disposable medium pressure preparative packed columns as described above that are previously packed with fillers and manufactured by Yamazen Corporation, Wako Pure Chemical Industries, Ltd., Biotage AB or W. R. Grace & Co. (Hi-Flash). The target compound whose purity is improved can be obtained by eluting the target compound with one or more solvents not reactive with the target compound using these silica gels, and distilling off the solvent(s).

When the collected target compound is a liquid, the purity of the target compound can also be improved by distillation. In distillation, the target compound can be distilled out by subjecting the target compound to reduced pressure at room temperature or under heating.

Representative examples of the method for producing Compound (1-1) or (1-2) have been described above. Raw material compounds and various reagents in the production of Compound (1-1) or (1-2) may form salts or solvates such as hydrates, all vary depending on the starting material, the solvent used or the like, and are not particularly limited insofar as they do not inhibit the reaction. Also, the solvent used varies depending on the starting material, the reagent or the like, and is not particularly limited insofar as it does not inhibit the reaction and dissolves the starting material to some degree, obviously. When Compound (1-1) or (1-2) is obtained as free form, it can be converted to a salt that may be formed by Compound (1-1) or (1-2) or solvate of the compound or salt by conventional methods.

When Compound (1-1) or (1-2) is obtained as a salt or solvate, it can be converted to free form of Compounds (1-1) or (1-2) by conventional methods.

Various isomers obtained for Compound (1-1) or (1-2) (such as geometric isomers, optical isomers, rotamers, stereoisomers and tautomers) can be purified and isolated using common separation means, for example, recrystallization, diastereomeric salt formation, enzymatic resolution and various chromatography methods (such as thin layer chromatography, column chromatography and gas chromatography).

Compound (1-1) or (1-2) or a pharmacologically acceptable salt thereof can be formulated by conventional methods, and examples of dosage forms include oral formulations (such as tablets, granules, powders, capsules and syrups), injections (for intravenous administration, intramuscular administration, subcutaneous administration and intraperitoneal administration) and external formulations (such as transdermal absorption formulations (such as ointments and patches), ophthalmic preparations, nasal preparations and suppositories).

These solid formulations such as tablets, capsules, granules and powders may contain usually 0.001 to 99.5 wt %, preferably 0.01 to 90 wt % or the like, of Compound (1-1) or (1-2) or a pharmacologically acceptable salt thereof.

When oral solid formulations are manufactured, tablets, granules, powders and capsules can be prepared by adding diluents, binders, disintegrants, lubricants, colorants or the like to Compound (1-1) or (1-2) or a pharmacologically acceptable salt thereof as necessary and treating by conventional methods. Tablets, granules, powders, capsules and the like may also be film coated as necessary.

Examples of diluents include lactose, corn starch and microcrystalline cellulose, examples of binders include hydroxypropylcellulose and hydroxypropylmethylcellulose, and examples of disintegrants include carboxymethylcellulose calcium and croscarmellose sodium.

Examples of lubricants include magnesium stearate and calcium stearate, and examples of colorants include titanium oxide.

Examples of film coating agents include hydroxypropylcellulose, hydroxypropylmethylcellulose and methylcellulose.

Any excipients described above are not limited to these examples, obviously

When injections (for intravenous administration, intramuscular administration, subcutaneous administration and intraperitoneal administration) are manufactured, they can be manufactured by adding pH adjusters, buffers, suspending agents, solubilizing agents, antioxidants, preservatives (antiseptics), tonicity adjusting agents or the like to Compound (1-1) or (1-2) or a pharmacologically acceptable salt thereof as necessary and treating by conventional methods. Lyophilized formulations to be dissolved before use may also be prepared by lyophilization. These injections can be administered intravenously, subcutaneously and intramuscularly, for example.

Examples of pH adjusters and buffers include organic acids or inorganic acids and/or salts thereof, examples of suspending agents include methylcellulose, polysorbate 80 and carboxymethylcellulose sodium, examples of solubilizing agents include polysorbate 80 and polyoxyethylene sorbitan monolaurate, examples of antioxidants include α-tocopherol, examples of preservatives include methyl parahydroxybenzoate and ethyl parahydroxybenzoate, and examples of tonicity adjusting agents include glucose, sodium chloride and mannitol; however, the excipients are not limited to these examples, obviously.

These injections may contain usually 0.000001 to 99.5 wt %, preferably 0.00001 to 90 wt % or the like, of Compound (1-1) or (1-2) or a pharmacologically acceptable salt thereof.

When external formulations are manufactured, transdermal absorption formulations (such as ointments and patches), ophthalmic preparations, nasal preparations, suppositories and the like can be manufactured by adding base materials and, as necessary, the emulsifiers, preservatives, pH adjusters, colorants and the like described above to Compound (1-1) or (1-2) or a pharmacologically acceptable salt thereof, and treating by conventional methods.

Various raw materials conventionally used for pharmaceuticals, quasi drugs, cosmetics and the like can be used as base materials, and examples include raw materials such as animal and vegetable oils, mineral oils, ester oils, waxes, higher alcohols and purified water.

These external formulations may contain usually 0.000001 to 99.5 wt %, preferably 0.00001 to 90 wt % or the like, of Compound (1-1) or (1-2) or a pharmacologically acceptable salt thereof.

The dosage of the medicine according to the present invention typically varies depending on the symptom, age, sex, weight or the like, but is acceptable if it is a dosage sufficient to produce a desired effect. For example, for an adult, a dosage of about 0.1 to 5000 mg (preferably 0.5 to 1000 mg, more preferably 1 to 600 mg) per day is used in one dose during one or more days or in 2 to 6 divided doses for one day.

Compound (1-1) or (1-2) can be used as a chemical probe to trap target proteins in bioactive low molecular weight compounds. Specifically, Compound (1-1) or (1-2) can be converted to an affinity chromatography probe, a photoaffinity probe or the like by introducing a labeling group, a linker or the like into a moiety differing from a structural moiety essential for expression of activity of the compound by a technique described in J. Mass Spectrum. Soc. Jpn., Vol. 51, No. 5, 2003, pp. 492-498 or WO 2007/139149 or the like.

Examples of labeling groups, linkers or the like used for chemical probes include groups shown in the group consisting of (1) to (5) below:
(1) protein labeling groups such as photoaffinity labeling groups (such as a benzoyl group, a benzophenone group, an azido group, a carbonylazido group, a diaziridine group, an enone group, a diazo group and a nitro group) and chemical affinity groups (such as a ketone group in which an a-carbon atom is replaced with a halogen atom, a carbamoyl group, an ester group, an alkylthio group, Michael receptors such as α,β-unsaturated ketones and esters, and an oxirane group),
(2) cleavable linkers such as —S—S—, —O—Si—O—, monosaccharides (such as a glucose group and a galactose group) or disaccharides (such as lactose), and oligopeptide linkers cleavable by enzymatic reaction,
(3) fishing tag groups such as biotin and a 3-(4,4-difluoro-5,7-dimethyl-4H-3a,4a-diaza-4-bora-s-indacen-3-yl)propionyl group,
(4) detectable markers such as radiolabeling groups such as $^{125}$I, $^{32}$P, $^{3}$H and $^{14}$C; fluorescence labeling groups such as fluorescein, rhodamine, dansyl, umbelliferone, 7-nitrofurazanyl and a 3-(4,4-difluoro-5,7-dimethyl-4H-3a,4a-diaza-4-bora-s-indacen-3-yl)propionyl group; chemiluminescent groups such as luciferin and luminol; and heavy metal ions such as lanthanoid metal ions and radium ions; or
(5) groups bound to solid phase carriers such as glass beads, glass beds, microtiter plates, agarose beads, agarose beds, polystyrene beads, polystyrene beds, nylon beads and nylon beds.

Probes prepared by introducing labeling groups or the like selected from the group consisting of (1) to (5) above into Compound (1-1) or (1-2) according to the method described in the above documents or the like can be used as chemical probes for identification of labeled proteins useful for searching for novel drug targets, for example.

EXAMPLES

Compound (1-1) or (1-2) can be produced by, for example, the methods described in the following examples and the effects of Compound (1-1) or (1-2) can be confirmed by the methods described in the following test examples. These are only illustrative, however, and the present invention is not in any way limited by these specific examples.

Example 1

N-(4-chloro-3-methyl-1,2-oxazol-5-yl)-2-[2-(6-methyl-1,3-dihydro-2-benzofuran-5-yl)acetyl]thiophene-3-sulfonamide

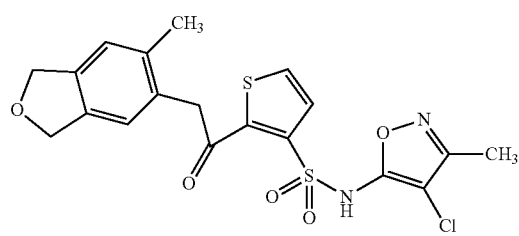 [SMILES: Cc1cc2c(cc1CC(=O)c1sccc1S(=O)(=O)Nc1onc(C)c1Cl)COC2]

A mixture of N-(4-chloro-3-methyl-1,2-oxazol-5-yl)-2-{2-[(6-methyl-1,3-dihydro-2-benzofuran-5-yl)methyl]-1,3-dithian-2-yl}thiophene-3-sulfonamide described in Production Example 1-7 (300 mg, 0.55 mmol), methanol (20 mL), water (2 mL) and silver nitrate (940 mg, 5.5 mmol) was stirred for 3 days at 55° C. The reaction mixture was allowed to cool to room temperature, tetrahydrofuran (40 mL) and brine (1 mL) were added at that temperature, and the mixture was filtered with Celite. The filtrate was extracted by addition of ethyl acetate (200 mL), water (100 mL) and saturated aqueous citric acid solution (1 mL). The organic layer was washed with brine and dried over anhydrous magnesium sulfate, and the solvent was distilled away under reduced pressure. The residue was purified by silica gel column chromatography (methanol:ethyl acetate=1:9), and then further purified by silica gel thin-layer chromatography (methanol:ethyl acetate=1:32) to give the title compound (45 mg, 18% yield).

¹H-NMR Spectrum (DMSO-d₆) δ (ppm): 1.99 (3H, s), 2.13 (3H, s), 4.89 (2H, s), 4.92 (2H, s), 4.95 (2H, s), 7.07 (1H, s), 7.09 (1H, s), 7.42 (1H, d, J=5.1 Hz), 7.77 (1H, d, J=5.1 Hz).

Production Example 1-1

[(4-chloro-3-methyl-1,2-oxazol-5-yl)sulfamoyl]thiophene-2-carboxylic acid

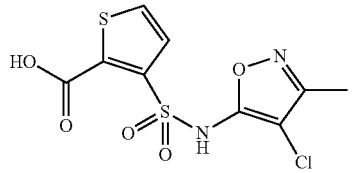 [SMILES: Cc1noc(NS(=O)(=O)c2ccsc2C(=O)O)c1Cl]

To a mixture of sodium hydride (60%, 2.1 g, 52 mmol) and tetrahydrofuran (20 mL) was added a mixture of 4-chloro-3-methyl-1,2-oxazol-5-amine (3.0 g, 23 mmol) and tetrahydrofuran (20 mL) at 0° C., followed by stirring at that temperature for 30 minutes. Methyl 3-(chlorosulfonyl)thiophene-2-carboxylate (5.3 g, 22 mmol) was added at that temperature to the reaction mixture, which was then stirred for 1 hour at 0° C., and then stirred for 4 hours at room temperature. Hexane (100 ml) was added at room temperature to the reaction mixture, and the precipitated solid was collected by filtration. Methanol (20 mL) was added to the solid, followed by a 2N aqueous solution of sodium hydroxide (20 mL), and the reaction mixture was stirred for 5 hours at room temperature. The solvent was distilled away under reduced pressure, and ice water (20 mL) was added to the residue, followed by a 2 N aqueous solution of hydrochloric acid (20 mL). The precipitated solid was collected by filtration to give the title compound (2.5 g, 35% yield).

¹H-NMR Spectrum (DMSO-d₆) δ (ppm): 2.16 (3H, d, J=1.8 Hz), 7.45 (1H, dd, J=1.3, 5.3 Hz), 7.95 (1H, dd, J=0.9, 5.3 Hz).

Production Example 1-2

3-[(4-chloro-3-methyl-1,2-oxazol-5-yl)sulfamoyl]-N-methoxy-N-methylthiophene-2-carboxamide

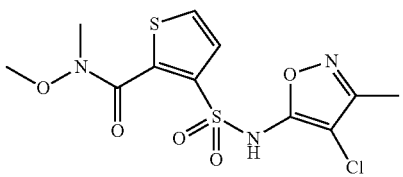

To a mixture of 3-[(4-chloro-3-methyl-1,2-oxazol-5-yl)sulfamoyl]thiophene-2-carboxylic acid (2.5 g, 7.8 mmol) described in Production Example 1-1 and tetrahydrofuran (25 mL) was added 1,1'-carbonyldiimidazole (2.0 g, 12 mmol) at room temperature, followed by stirring at that temperature for 30 minutes. Imidazole (1.1 g, 16 mmol) and N,O-dimethylhydroxylamine hydrochloride (1.2 g, 12 mmol) were added successively at room temperature to the reaction mixture, followed by stirring at that temperature for 5 hours. A 1 N aqueous solution of hydrochloric acid (50 mL) was added to the reaction mixture, which was then extracted with ethyl acetate. The organic layer was washed with brine and dried over anhydrous sodium sulfate, and the solvent was distilled away under reduced pressure. The residue was purified by silica gel column chromatography (chloroform:methanol=9:1) to give the title compound (1.5 g, 53% yield).

¹H-NMR Spectrum (CDCl₃) δ (ppm): 2.23 (3H, s), 3.45 (3H., s), 3.74 (3H, s), 7.47 (1H, d, J=5.3 Hz), 7.53 (1H, d, J=5.3 Hz).

Production Example 1-3

N-(4-chloro-3-methyl-1,2-oxazol-5-yl)-2-formylthiophene-3-sulfonamide

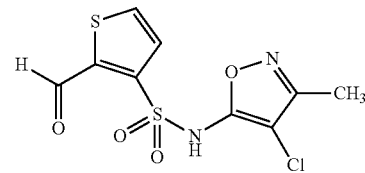 [SMILES: Cc1noc(NS(=O)(=O)c2ccsc2C=O)c1Cl]

To a mixture of 3-[(4-chloro-3-methyl-1,2-oxazol-5-yl)sulfamoyl]-N-methoxy-N-methylthiophene-2-carboxamide described in Production Example 1-2 (8.0 g, 22 mmol) and tetrahydrofuran (160 mL), was added dropwise diisobutyl aluminum hydride (46 mL, 48 mmol, 1.0 M n-hexane solution) at −78° C., followed by stirring at 0° C. for 30 minutes. A saturated aqueous solution of ammonium chloride was added dropwise at 0° C. to the reaction mixture, which was then gradually allowed to warm to room temperature and stirred for 1 hour at that temperature. The reaction mixture was filtered with Celite, and water was added to the filtrate, which was then extracted with ethyl acetate. The organic layer was washed with brine, and the solvent was distilled away under reduced pressure. The residue was purified by silica gel column chromatography (ethyl acetate:methanol=30:1) to give the title compound (5.1 g, 75% yield).

¹H-NMR Spectrum (DMSO-d₆) δ (ppm): 1.97 (3H, s), 7.35 (1H, d, J=5.1 Hz), 7.97 (1H, d, J=5.1 Hz), 10.52 (1H, d, J=1.1 Hz).

Production Example 1-4

5,11-dioxatricyclo[7.3.0.0^{3,7}]dodeca-1,3(7),8-triene

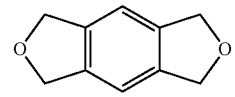 [SMILES: c1c2c(cc3c1COC3)COC2]

To a mixture of 1,2,4,5-tetrakis-(bromomethyl)-benzene (150 g, 0.33 mmol) and 1,4-dioxane (2 L) was added a 55% aqueous solution of tetrabutylammonium hydroxide (640 mL) at room temperature, followed by stirring at 90° C. for 6 hours. The reaction mixture was allowed to cool to room temperature, and extracted with ethyl acetate after addition of a 2 N aqueous solution of hydrochloric acid (2 L). The organic layer was washed with brine and dried over anhydrous sodium sulfate, and the solvent was distilled away under reduced pressure. The residue was purified by silica gel column chromatography (ethyl acetate:hexane=1:9) to give the title compound (35 g, 63% yield).

$^1$H-NMR Spectrum (CDCl$_3$) δ (ppm): 5.10 (8H, s), 7.08 (2H, s).

Production Example 1-5

(6-methyl-1,3-dihydro-2-benzofuran-5-yl) methanol

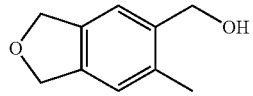

To a mixture of lithium powder (15 g, 2.1 mol), 4,4'-di-tert-butylbiphenyl (5.0 g, 0.021 mol) and tetrahydrofuran (200 mL) was added a mixture of 5,11-dioxatricyclo[7.3.0.0^{3,7}]dodeca-1,3(7),8-triene (35 g, 0.21 mol) described in Production Example 1-4 and tetrahydrofuran (100 mL) at −78° C., followed by stirring at that temperature for 4 hours. Water (10 mol) was added at that temperature to the reaction mixture, and thoroughly stirred. The reaction mixture was allowed to warm to room temperature, and extracted with ethyl acetate after addition of a 2 N aqueous solution of hydrochloric acid (500 mL). The organic layer was washed with brine and dried over anhydrous sodium sulfate, and the solvent was distilled away under reduced pressure. The residue was purified by silica gel column chromatography (ethyl acetate:hexane=3:7) to give the title compound (10 g, 30% yield).

$^1$H-NMR Spectrum (DMSO-d$_6$) δ (ppm): 2.24 (3H, s), 4.48 (2H, d, J=5.3 Hz), 4.96 (4H, s), 5.10 (1H, t, J=5.3 Hz), 7.07 (1H, s), 7.29 (1H, s).

Production Example 1-6

5-(chloromethyl)-6-methyl-1,3-dihydro-2-benzofuran

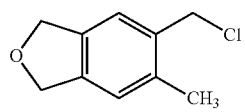

Triethylamine (1.7 mL, 12 mmol) was added under ice cooling to a mixture of (6-methyl-1,3-dihydro-2-benzofuran-5-yl)methanol described in Production Example 1-5 (1.0 g, 6.1 mmol) and dichloromethane (10 mL), followed by the addition of methanesulfonyl chloride (470 μL, 6.1 mmol) at that temperature. The reaction mixture was stirred for 3 hours at room temperature. Water was added to the reaction mixture, which was then extracted with ethyl acetate. The organic layer was washed with brine and dried over anhydrous magnesium sulfate, and the solvent was distilled away under reduced pressure. The residue was purified by silica gel column chromatography (ethyl acetate:heptane=1:10) to give the title compound (680 mg, 61% yield).

$^1$H-NMR Spectrum (CDCl$_3$) δ (ppm): 2.44 (3H, s), 4.63 (2H, s), 5.08 (4H, s), 7.09 (1H, s), 7.20 (1H, s).

Production Example 1-7

N-(4-chloro-3-methyl-1,2-oxazol-5-yl)-2-{2-[(6-methyl-1,3-dihydro-2-benzofuran-5-yl)methyl]-1,3-dithian-2-yl}thiophene-3-sulfonamide

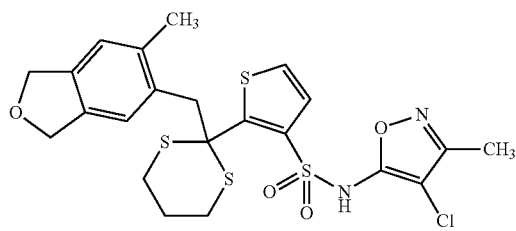 [SMILES: Cc1cc2c(cc1CC1(c3sccc3S(=O)(=O)Nc3onc(C)c3Cl)SCCCS1)COC2]

To a mixture of N-(4-chloro-3-methyl-1,2-oxazol-5-yl)-2-formylthiophene-3-sulfonamide described in Production Example 1-3 (4.9 g, 16 mmol) and dichloromethane (100 mL) was successively added boron trifluoride diethyl etherate (8.1 mL, 64 mmol) and 1,3-propanedithiol (1.9 mL, 19 mmol) under ice cooling, followed by stirring at room temperature for 90 minutes. Water was added under ice cooling to the reaction mixture, which was then extracted with dichloromethane. The organic layer was washed with brine, and the solvent was distilled away under reduced pressure. The residue was purified by silica gel column chromatography (ethyl acetate) to give N-(4-chloro-3-methyl-1,2-oxazol-5-yl)-2-(1,3-dithian-2-yl)thiophene-3-sulfonamide as a crude product. To a mixture of crude N-(4-chloro-3-methyl-1,2-oxazol-5-yl)-2-(1,3-dithian-2-yl)thiophene-3-sulfonamide and tetrahydrofuran (50 mL) was added dropwise n-butyl lithium (9.7 mL, 16 mmol, 1.6 M n-hexane solution) at −78° C., followed by stirring for 20 minutes at an internal temperature of −35° C. The reaction mixture was cooled to −78° C., and 5-(chloromethyl)-6-methyl-1,3-dihydro-2-benzofuran described in Production Example 1-6 (960 mg, 5.3 mmol) was added at that temperature and stirred for 1 hour at 0° C. The reaction mixture was cooled to −78° C., and a mixture of acetic acid (0.90 mL, 16 mmol) and tetrahydrofuran (7 mL) was added at that temperature. The reaction mixture was gradually returned to room temperature, water and an aqueous citric acid solution were added at that temperature, and the mixture was extracted with ethyl acetate. The organic layer was washed with brine, and the solvent was distilled away under reduced pressure. The residue was purified by silica gel column chromatography (ethyl acetate:heptane=4:1) to give the title compound (1.6 g, 54% yield).

$^1$H-NMR Spectrum (DMSO-d$_6$) δ (ppm): 1.68-1.76 (1H, m), 2.01-2.05 (1H, m), 2.15 (3H, s), 2.20 (3H, s), 2.80-2.85 (4H, m), 3.73 (2H, s), 4.79 (2H, s), 4.90 (2H, s), 6.64 (1H, s), 7.02 (1H, s), 7.44 (1H, d, J=5.5 Hz), 7.54 (1H, d, J=5.5 Hz).

Test Example 1

Suppression effects of sitaxentan and the compound of Example 1 on endothelin receptor A (EDNRA)

The protein coding region of human derived EDNRA (gene number NM_001957.2) was transduced into HEK-293 (Human Embryonic Kidney, ATCC No. CRL-1573) cells with a murine leukemia retrovirus vector, to prepare a cell line stably expressing EDNRA (EDNRA/293 cells). DMEM (Dulbecco's Modified Eagle Medium) supplemented with 10% fetal bovine serum and penicillin and streptomycin was used as the culture medium.

One day before measurement, the EDNRA/293 cells were inoculated on a 384-well plate at 5000 cells/well. On the day of measurement, a fluorescent reagent for calcium measurement (Calcium4, Molecular Device) dissolved in Hanks balanced buffer solution was added to each well, and allowed standing for about 1 hour. Sitaxentan and the compound of Example 1 prepared to predetermined final concentrations (hereunder called the specimens) were then added to some of the wells, and allowed standing for about 1 hour to allow the specimens to act on the EDNRA/293

Endothelin, an EDNRA ligand (activator) was applied to the wells not treated with the specimens, and the resulting activation (calcium elevation) reaction was detected by a measuring instrument (FDSS7000, Hamamatsu Photonics) to obtain a dose-dependent activation reaction as shown in FIG. 1. At doses of 1 nM or more, the activation reaction became almost saturated. For this reason, the doses of endothelin used for detection in the suppression reactions below were set at 0.03, 0.1 or 0.3 nM.

Figure 2:
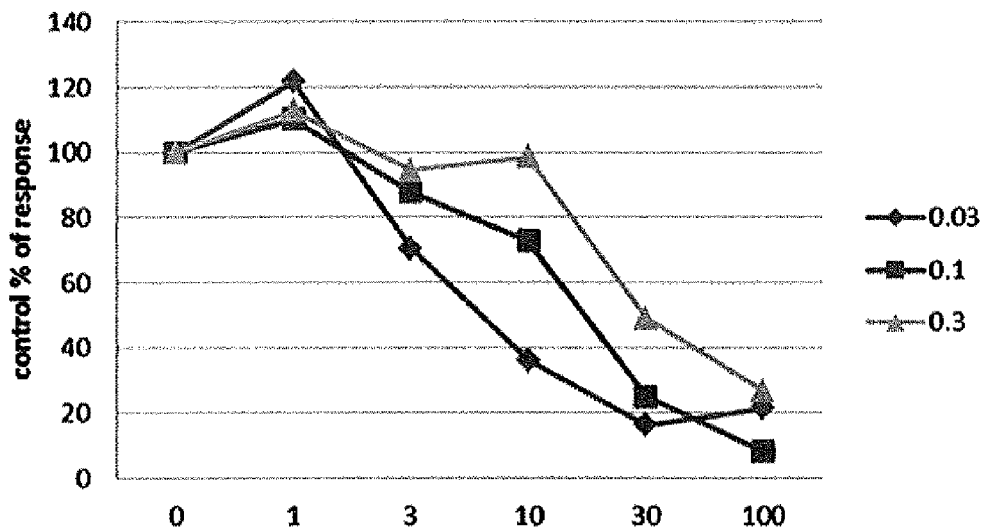
FIG. 2 is a graph showing dose-dependent suppression of $Ca^{2+}$ elevation in EDNRA/293 cells by sitaxentan, relative $Ca^{2+}$ elevation given 100% as the value without sitaxentan is shown on the vertical axis, while sitaxentan concentration (nM) is shown on the horizontal axis, and the endothelin concentrations (nM) are shown to the right of the graph.
Figure 3:
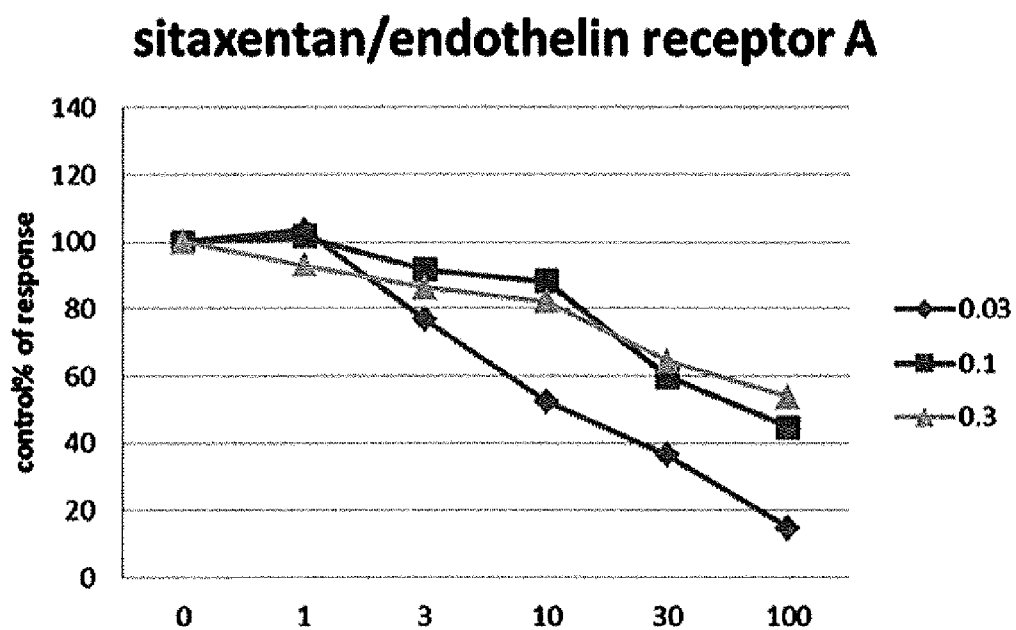
FIG. 3 is a graph showing dose-dependent suppression of $Ca^{2+}$ elevation in EDNRA/293 cells by the compound of Example 1, relative $Ca^{2+}$ elevation given 100% as the value without the compound of Example 1 is shown on the vertical axis, while the concentration of the compound of Example 1 is (nM) is shown on the horizontal axis, and the endothelin concentrations (nM) are shown to the right of the graph.

When the activation (calcium elevation) reaction that occurred when 0.03, 0.1 or 0.3 nM of endothelin was applied to separate wells treated with the specimens was detected by a measurement instrument (FDSS7000, Hamamatsu Photonics), both sitaxentan and the compound of Example 1 suppressed the activation reaction as shown in FIG. 2 and FIG. 3.

Test Example 2

CYP Inhibitory Effects

The CYP inhibitory effects of sitaxentan and the compound of Example 1 were tested by the following two methods.

Because time-dependent inhibition of CYP by sitaxentan can be evaluated by testing the increase in inhibition after pre-incubation with a solution containing a coenzyme and a human hepatic microsomal fraction containing CYP, a time-dependent inhibition test was performed for the compound of Example 1 as Method 1. Competitive inhibition of CYP was also tested as Method 2.

Method 1

The time-dependent inhibition abilities of sitaxentan and the compound of Example 1 were evaluated with respect to five CYP enzymes (CYP1A2, 2C9, 2C19, 2D6 and 3A4).

The test substance was added to an enzyme solution (containing human hepatic microsome (0.2 mg/mL), 100 mM Kpi and 0.1 mM EDTA), and pre-incubated for 30 minutes at 37° C. in the presence of or absence of the coenzyme. The final concentration of the test substance was set at 0.1, 0.2, 0.4, 0.5, 1, 2, 10 or 50 μM. A NADPH generating system (60 mM MgCl$_2$ solution containing 3.6 mM β-NADP$^+$, 90 mM glucose-6-phosphate and 1 Unit/mL glucose-6-phosphate dehydrogenase, incubated for 5 minutes to generate NADPH) was used as the coenzyme. After pre-incubation, part of the reaction solution was collected, diluted 10 times by mixing with a model substrate solution and the NADPH generating system, and then incubated for 10 minutes at 37° C. An equal amount of a mixed solution of acetonitrile and methanol (1:1, containing 0.05 μM dextrophan or 0.05 μM propranolol as an internal standard) was added to terminate the reaction, and metabolites of the model substrate in the reaction solution were measured by LC-MS/MS. The model substrates and model substrate metabolites for each CYP enzyme are shown in Table 1. A similar test was also performed with no test substance added as a control test. The ratio relative to the amount of model substrate metabolites in the control test was given as residual activity. The ratio of residual activity in the presence of NADPH relative to residual activity in the absence of NADPH was evaluated, and the ratio of 80% or less was defined "+", while the ratio of above 80% was defined as "−". The results are shown in Table 2.

It can be seen from a comparison of the results of sitaxentan and the compound of Example 1 that time-dependent inhibition was reduced by converting the benzodioxol ring to a phthalan ring.

TABLE 1

Model substrates and model substrate metabolites for each CYP enzyme

| CYP isoform | Model substrate | Substrate concentration (μM) | Model substrate metabolite |
| --- | --- | --- | --- |
| CYP1A2 | Phenacetin | 50 | Acetaminophen |
| CYP2C9 | Tolbutamide | 500 | 4-Hydroxytolbutamide |
| CYP2C19 | S-Mephenytoin | 200 | 4'-Hydroxymephenytoin |
| CYP2D6 | Bufuralol | 50 | 1'-Hydroxybufuralol |
| CYP3A4 | Midazolam | 30 | 1'-Hydroxymidazolam |

TABLE 2

Effect of pre-incubation with human hepatic microsome and test substance on CYP activity (average, n = 2)

| Test substance | Concentration (μM) | CYP1A2 | CYP2C9 | CYP2C19 | CYP2D6 | CYP3A4 |
| --- | --- | --- | --- | --- | --- | --- |
| Sitaxentan | 10 | − | + | + | − | + |
|  | 50 | + | + | + | + | + |
| Example 1 | 10 | − | − | − | − | − |
|  | 50 | − | − | − | − | + |

Method 2

Inhibition ability based on competitive inhibition of five CYP enzymes (CYP1A2, 2C9, 2C19, 2D6 and 3A4) was evaluated using sitaxentan and the compound of Example 1.

The test substance was added at a final concentration of 1 or 10 μM to an enzyme solution (containing human hepatic microsome (0.2 mg/mL), 100 mM Kpi and 0.1 mM EDTA) containing a model substrate solution, and incubated for 10 minutes at 37° C. in the presence of an NADPH generating system. An equal amount of a mixed solution of acetonitrile and methanol (1:1, containing 0.05 μM dextrophan or 0.05 μM propranolol as an internal standard) was added to terminate the reaction, and metabolites of the model substrate in the reaction solution were measured by LC-MS/MS. The model substrate and model substrate metabolite for each CYP enzyme are shown in Table 3. A similar test was performed without addition of the test substance as a control test. The inhibition rate was determined from the amounts of model substrate metabolites with and without addition of the test substance at each test substance concentration, and the $IC_{50}$ value was calculated from the inhibition rate (calculation method in accordance with Xenobiotica, 1999, 29(1), 53-75). A score of "++H-" was given if the $IC_{50}$ was 1 μM or less, "+" if it was 1 to 10 μM, and "−" if it was greater than 10 μM. The results are shown in Table 4.

It can be seen from a comparison of the results for sitaxentan and the compound of Example 1 that inhibition ability was weakened by converting the benzodioxol ring to a phthalan ring.

TABLE 3

Model substrates and model substrate metabolites for CYP enzymes

| CYP isoform | Model substrate | Substrate concentration (μM) | Model substrate metabolite |
|---|---|---|---|
| CYP1A2 | Phenacetin | 10 | Acetaminophen |
| CYP2C9 | Tolbutamide | 100 | 4-Hydroxytolbutamide |
| CYP2C19 | S-Mephenytoin | 40 | 4'-Hydroxymephenytoin |
| CYP2D6 | Bufuralol | 10 | 1'-Hydroxybufuralol |
| CYP3A4 | Midazolam | 3 | 1'-Hydroxymidazolam |

TABLE 4

Effect of test substance on CYP enzymes (n = 2)

| Test substance | CYP1A2 | CYP2C9 | CYP2C19 | CYP2D6 | CYP3A4 |
|---|---|---|---|---|---|
| Sitaxentan | − | ++ | + | − | + |
| Example 1 | − | ++ | − | − | − |

The invention claimed is:

1. A compound represented by formula (1-1) or formula (1-2), or a pharmacologically acceptable salt thereof:

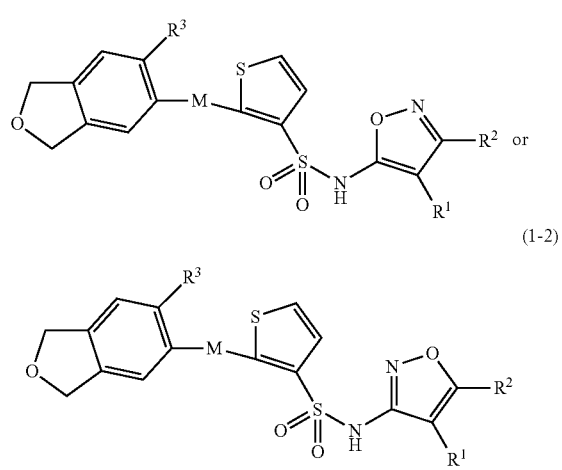

wherein $R^1$ is a halogen atom, a methyl group, an ethyl group, a trifluoromethyl group, a pentafluoroethyl group, an n-propyl group or a cyclopropyl group,
$R^2$ is a hydrogen atom, a methyl group, an ethyl group, a trifluoromethyl group, a pentafluoroethyl group, an n-propyl group or a cyclopropyl group,
$R^3$ is a $C_{1-6}$ alkyl group or a $C_{1-6}$ alkoxy group, and
M is a group selected from the group consisting of:

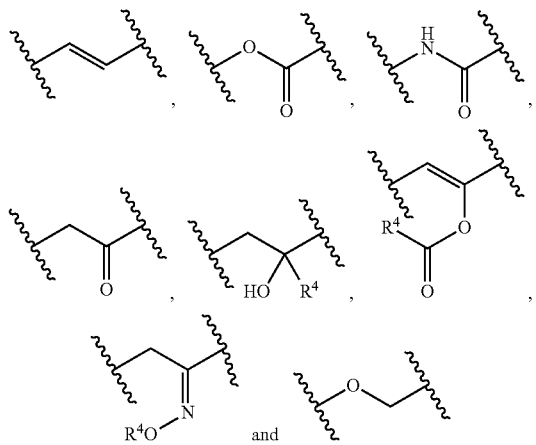

wherein $R^4$ is a hydrogen atom, a methyl group or an ethyl group.

2. The compound or pharmacologically acceptable salt thereof according to claim 1, wherein M is a group represented by the following formula:

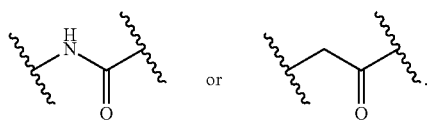 [SMILES: *NC(*)=O ; *CC(*)=O]

3. The compound or pharmacologically acceptable salt thereof according to claim 1, wherein M is a group represented by the following formula:

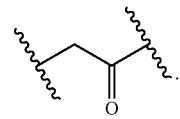 [SMILES: *CC(*)=O]

4. The compound or pharmacologically acceptable salt thereof according to claim 1, wherein $R^1$ is a halogen atom.

5. The compound or pharmacologically acceptable salt thereof according to claim 4, wherein $R^1$ is a chlorine atom.

6. The compound or pharmacologically acceptable salt thereof according to claim 1, wherein $R^2$ is a methyl group.

7. The compound or pharmacologically acceptable salt thereof according to claim 1, wherein $R^3$ is a $C_{1-6}$ alkyl group.

8. The compound or pharmacologically acceptable salt thereof according to claim 7, wherein $R^3$ is a methyl group.

9. The compound or pharmacologically acceptable salt thereof according to claim 1, which is a compound represented by formula (1-1).

10. N-(4-Chloro-3-methyl-1,2-oxazol-5-yl)-2-[2-(6-methyl-1,3-dihydro-2-benzofuran-5-yl)acetyl]thiophene-3-sulfonamide or a pharmacologically acceptable salt thereof.

11. A pharmaceutical composition comprising the compound or pharmacologically acceptable salt thereof according to claim 1.

12. A method of antagonizing an endothelin receptor comprising administering the compound or pharmacologically acceptable salt thereof according to claim 1 to a patient in need thereof.

13. A method of treating pulmonary arterial hypertension comprising administering the compound or pharmacologically acceptable salt thereof according to claim 1 to a patient in need thereof.

14. A pharmaceutical composition comprising the compound N-(4-Chloro-3-methyl-1,2-oxazol-5-yl)-2-[2-(6-methyl-1,3-dihydro-2-benzofuran-5-yl)acetyl]thiophene-3-sulfonamide or pharmacologically acceptable salt thereof according to claim 10.

15. A method of antagonizing an endothelin receptor comprising administering the compound N-(4-Chloro-3-methyl-1,2-oxazol-5-yl)-2-[2-(6-methyl-1,3-dihydro-2-benzofuran-5-yl)acetyl]thiophene-3-sulfonamide or pharmacologically acceptable salt thereof according to claim 10 to a patient in need thereof.

16. A method of treating pulmonary arterial hypertension comprising administering the compound N-(4-Chloro-3-methyl-1,2-oxazol-5-yl)-2-[2-(6-methyl-1,3-dihydro-2-benzofuran-5-yl)acetyl]thiophene-3-sulfonamide or pharmacologically acceptable salt thereof according to claim 10 to a patient in need thereof.

\* \* \* \* \*